United States Patent
Hill et al.

(10) Patent No.: US 9,759,640 B2
(45) Date of Patent: Sep. 12, 2017

(54) BIOLOGICAL SAMPLE COLLECTION AND PRESERVATION

(71) Applicant: Spot on Sciences, Inc., Austin, TX (US)

(72) Inventors: James Hill, Manor, TX (US); Jeanette Hill, Manor, TX (US)

(73) Assignee: Spot on Sciences, Inc., Austin, TX (US)

( * ) Notice: Subject to any disclaimer, the term of this patent is extended or adjusted under 35 U.S.C. 154(b) by 0 days.

(21) Appl. No.: 14/776,299

(22) PCT Filed: Mar. 14, 2014

(86) PCT No.: PCT/US2014/029440
§ 371 (c)(1),
(2) Date: Sep. 14, 2015

(87) PCT Pub. No.: WO2014/153181
PCT Pub. Date: Sep. 25, 2014

(65) Prior Publication Data
US 2016/0033373 A1 Feb. 4, 2016

Related U.S. Application Data

(60) Provisional application No. 61/782,393, filed on Mar. 14, 2013.

(51) Int. Cl.
| | |
|---|---|
| *A61B 10/02* | (2006.01) |
| *A61B 10/00* | (2006.01) |
| *G01N 1/30* | (2006.01) |
| *B01L 3/02* | (2006.01) |
| *B01L 3/00* | (2006.01) |

(Continued)

(52) U.S. Cl.
CPC ............ *G01N 1/30* (2013.01); *A61B 10/0038* (2013.01); *A61B 10/0096* (2013.01); *A61B 10/0233* (2013.01); *A61B 10/0266* (2013.01); *B01L 3/0231* (2013.01); *B01L 3/5023* (2013.01); *B01L 3/5055* (2013.01); *G01N 1/08* (2013.01); *G01N 1/31* (2013.01); *A61B 10/0241* (2013.01); *B01L 2200/141* (2013.01);
(Continued)

(58) Field of Classification Search
None
See application file for complete search history.

(56) References Cited

U.S. PATENT DOCUMENTS

| | | |
|---|---|---|
| 7,601,546 B2 | 10/2009 | Bayloff et al. |
| 7,914,461 B2 | 3/2011 | Richard et al. |

(Continued)

FOREIGN PATENT DOCUMENTS

WO WO-2012/027048 A2 3/2012

*Primary Examiner* — Laura Schuberg
(74) *Attorney, Agent, or Firm* — Winstead PC

(57) ABSTRACT

An embodiment of the claimed invention is directed to a method that greatly streamlines and reduces costs for tissue preparation, preservation, long-term storage and sample retrieval for molecular analysis using a method based on dried blood spot (DBS) technology. In this method, a small needle punch sample of freshly excised tissue will be homogenized in stabilizing reagent and inserted into a device containing absorbent material and drying agent. This device is suitable for long-term sample storage at ambient temperature and allows for easy removal of sections for biomarker analysis.

4 Claims, 4 Drawing Sheets

(51) Int. Cl.
  *G01N 1/08* (2006.01)
  *G01N 1/31* (2006.01)
  *G01N 1/40* (2006.01)

(52) U.S. Cl.
  CPC . *B01L 2300/0803* (2013.01); *B01L 2300/105* (2013.01); *G01N 2001/4027* (2013.01)

(56) References Cited

U.S. PATENT DOCUMENTS

| | | | |
|---|---|---|---|
| 9,040,236 B2 * | 5/2015 | Hill | A61B 5/15142 422/547 |
| 2006/0018799 A1 | 1/2006 | Wong et al. | |

* cited by examiner

BIOLOGICAL SAMPLE COLLECTION AND PRESERVATION

CROSS-REFERENCES TO RELATED APPLICATIONS

This application claims the benefit under 35 U.S.C. §119(e) of U.S. Provisional Patent Application No. 61/782,393 filed Mar. 14, 2013 which is incorporated herein by reference in its entirety as if fully set forth herein.

STATEMENT REGARDING FEDERALLY SPONSORED RESEARCH OR DEVELOPMENT

This invention was made with government support under W31P4Q-11-C-0234 awarded by Defense Advanced Research Projects Agency (DARPA). The government has certain rights in the invention.

BACKGROUND OF THE INVENTION

The collection, preservation and storage of tissue samples for molecular analysis is essential for cancer treatment and for research and development of tissue-based biomarkers for disease pathophysiology. Much effort is currently focused on determining markers based on nucleotides (i.e. DNA, mRNA, miRNA), proteins and metabolites for cancer staging, prognosis and treatment selection. Detection of these biomarkers would more efficiently direct patients to treatments with the highest potential for benefit.

Current tissue preservation methods such as formalin-fixed, paraffin embedded (FFPE) are suitable for histopathology studies but not amenable to biomarker analysis due to poor protein and nucleic acid recovery. Even though recent reports describe some success with genetic analysis, the poor quality of DNA and RNA restricts analysis by common techniques such as RT-PCR, microarrays and sequencing. Extraction of full-length, non-degraded, immunoreactive proteins from FFPE tissue has also proved challenging, with limited detection by common methods such as ELISA and bead-based multiplexed immunoassays.

Another tissue preservation method, snap-freezing of sectioned tissue samples in liquid nitrogen followed by storage at −80° C., has proved more successful for long-term tissue storage and protein and DNA analysis. While this method may be suitable for limited sampling, it is not practical for wide-scale use due to high costs and infrastructure requirements as well as logistical issues in collecting, maintaining and shipping samples at sub-freezing temperatures.

A major limitation for disease and biomarker research is a lack of robust and relevant biological samples. Small collections of biological samples are spread throughout research institutions, but sample collection and storage is not uniform and samples are often compromised, which can lead to faulty data. As a key recent example, NCI attempted to form a cancer biobank through the Cancer Genome Atlas program but found that up to 99% of stored blood and tissue samples were unacceptable for research.

The development of alternative methods for simplified tissue sample storage has proved challenging. Meanwhile, methods for blood specimen collection and storage are undergoing a revolution to a new method, known as dried blood spot (DBS) sampling, which offers considerable advantages over traditional venipuncture including decreased costs, reduced sample size and increased analyte stability. Using a finger or neonatal heel stick, approximately 100 µL of blood is spotted onto a filter paper and dried at ambient temperature. Once dried, analytes including DNA/RNA, proteins and small molecules are stable at ambient temperature or under refrigeration for years. We recently demonstrated that detection of miRNA levels were equivalent between wet and dried blood. Analytes are extracted from the paper with solvent and measured by traditional methods including LC-MS/MS, RT-PCR, microarray, ELISA, etc.

Similar to dried blood, suspensions of tumor cells dried on filter paper show RNA and DNA stability for at least six months and suitability for PCR-based analysis, suggesting that dried tissue may also provide long-term stability. It would therefore be desirable to have a system that would provide for the collection, preservation and long-term storage of biological tissue samples in order to enable wide range testing of the samples that are not possible with currently existing methodologies.

SUMMARY OF THE INVENTION

The present invention generally relates to the collection, preservation and storage of biological samples as a dried homogenate for subsequent testing. More particularly, the present invention is concerned with a method and apparatus for a single use collection of a biological sample, homogenization and storage of a dried sample.

An embodiment of the invention is directed to a device, wherein the device comprises: a tube that contains a removable punch biopsy needle that fits within the tube; and a homogenization device that is located within the chamber of the tube at a location that is distal to the location of the needle, wherein the homogenization device is accessible to tissue delivery.

A further embodiment of the invention is directed to a method of extracting and storing a biological sample the method comprising the step of: retrieving a tissue sample by extracting the sample from a specimen; contacting the tissue sample with a buffer; homogenizing the tissue sample with a homogenization device to produce a liquid homogenate; transferring the liquid homogenate on to an absorbent material; and drying the liquid homogenate on the absorbent material to create a storable sample at ambient temperature.

DETAILED DESCRIPTION OF EXEMPLARY EMBODIMENTS

An embodiment of the invention is directed to the sampling, processing and storage of tissue specimens.

In accordance with an embodiment of the invention, a tube-like device is used to sample a portion of a tissue specimen. In this embodiment, the device is adapted to contain a needle that is used to punch or collect a sample of a tissue specimen. In certain embodiments of the invention, the size of the sample that is collected with the device is around 3 mm However, it should be recognized that the size of the sample will largely be dependent upon the uses that the sampled tissue specimen will be subjected to. In certain embodiments of the invention the tube-like device is a syringe or a syringe-like device.

Figure 1:
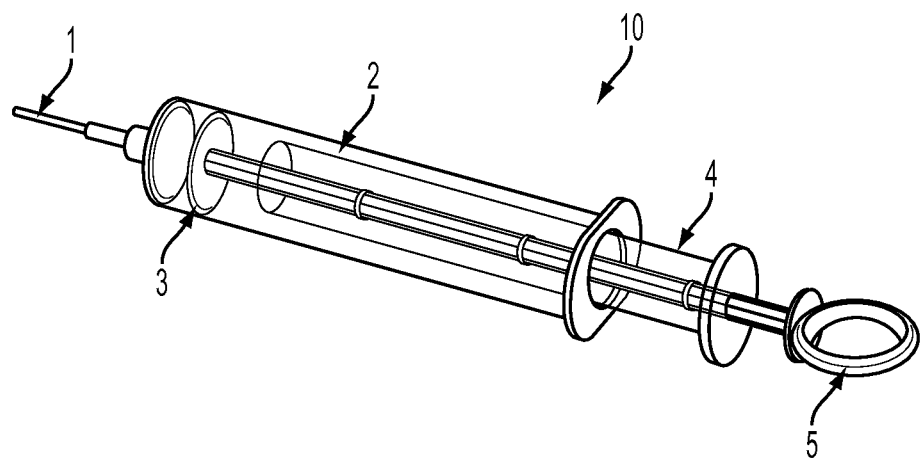
FIG. 1 is directed to a device in accordance with an embodiment of the invention.

As shown in FIG. 1, a device 10 in accordance with an embodiment of the invention comprises a tube (2) that is adapted to have a needle (1) at its proximate end and a plunger at its distal end. In certain embodiments of the invention, the plunger that is used is a double plunger, which comprises first (4) and second (5) plungers that slide in opposite directions within the syringe. The device is constructed so that only one plunger can be employed at a time. The first plunger (4) is designed to aid in the collection of the tissue specimen. The device further comprises a grating plate (3) that is located within the chamber of the tube 2 at a location that is distal to the location of the needle. The grating plate is distally connected to the second plunger (5), which aids in the homogenization of the collected sample. In other embodiments of the invention, the homogenization step is carried out by friction-based homogenization or blade-type homogenization (i.e. a blender or chopper). In certain embodiments of the invention, the first plunger 4 is an outer plunger and the second plunger 5 is an inner plunger. In certain embodiments of the invention, the tube 2 can be a cylindrical tube or a syringe.

Figure 2:
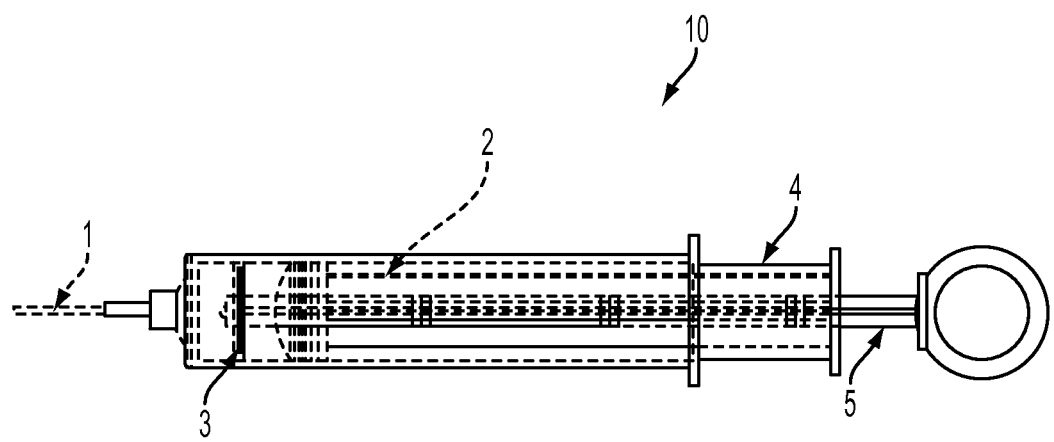
FIG. 2 is directed to a device in accordance with an embodiment of the invention.

FIG. 2 shows a cross-section of the device 10 set forth in FIG. 1 with the various components labeled similarly to FIG. 1.

Figure 3:
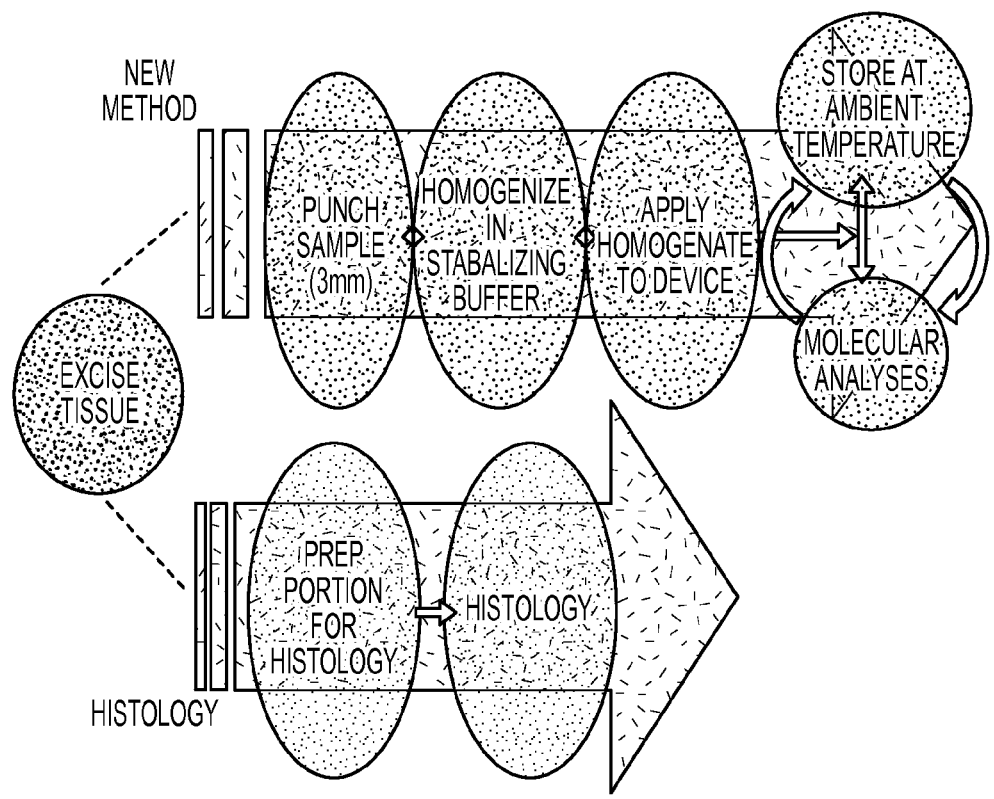
FIG. 3 shows a process flow of an exemplary method in accordance with an embodiment of the invention.

As shown in FIG. 3, in an embodiment of the invention, a sample of a tissue specimen is retrieved by using the needle (1) to punch the specimen and extract a sample by using the first plunger (4) to draw the sample into the tube (2). After the sample has been extracted and drawn into the syringe, a stabilizing buffer is introduced to the sample. The buffer can be introduced to the sample by withdrawing it from a buffer source using the first plunger (4). After the buffer has contacted the sample, the grating plate (3) is used to homogenize the sample using the second plunger (5). Examples of the homogenization buffer include aqueous buffers such as phosphate buffers and PBS containing protease inhibitors, RNAse inhibitors, detergents and organic solvents.

Following the homogenization step, the liquid homogenate is stored in a manner that facilitates future testing of the samples. In an embodiment of the invention, the liquid homogenate is applied to a surface of an absorbent material. The purpose of applying the liquid homogenate to the absorbent material is to enable the absorbent material to function as a storage medium for the homogenized sample.

In an embodiment of the invention, the absorbent material containing the liquid homogenate is transferred to a receptacle containing a drying agent. The drying agent facilitates the removal of moisture from the absorbent material. Upon removal of the moisture from the sample, the specimen sample is adsorbed on the surface of the absorbent material and can be stored at ambient temperature. The dried absorbent material can now be used for testing of the specimen.

Figure 4:
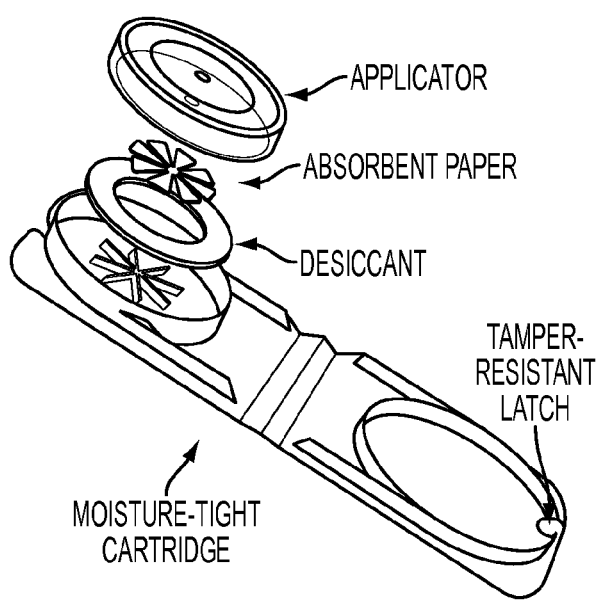
FIG. 4 shows a drawing of the HemaSpot cartridge.

In an embodiment of the invention, the liquid homogenate is applied to a collection cartridge (FIG. 4). In an embodiment of the invention, the collection cartridge is the HemaSpot™ collection device. This device comprises absorbent paper that is adjacent to a dessicant that permits the drying the sample on the absorbent paper.

The remaining excised tissue is examined by traditional histological or other methods requiring intact tissue and cellular structure.

Biological samples that can be manipulated with the device of the claimed invention include, but are not limited to:

1. Biopsied tissue including tumors of liver, skin, kidney, heart, brain, ovaries, and prostate.
2. Fecal matter (to identify intestinal flora)
3. Plant tissue (i.e. food: vegetables, fruits; crops, trees, flowers)—to identify species, phenotype, viral/bacterial infection
4. Meat—identify species, contamination
5. Forensic tissue—identify DNA; and
5. Soil samples Success of this dried tissue spot method would be a significant improvement over current tissue methods. Possible advantages as compared to current FFPE and flash freezing methods are outlined in Table 1 below.

TABLE 1

| Feature | FFPE | Flash Freeze | Dried Tissue |
|---|---|---|---|
| 1. Non-hazardous sample prep | x | x | ✓ |
| 2. Minimum infrastructure needs | x | x | ✓ |
| 3. Prep time <60 minutes | x | ✓ | ✓ |
| 4. Storage at ambient temp. | ✓ | x | ✓ |
| 5. Simple sample shipment | x | x | ✓ |
| 6. Efficient protein recovery | x | ✓ | ✓ |
| 7. Efficient nucleotide recovery | x | ✓ | ✓ |
| 8. Ease of sample prep & analysis | x | x | ✓ |

WORKING EXAMPLES

Figure 5:
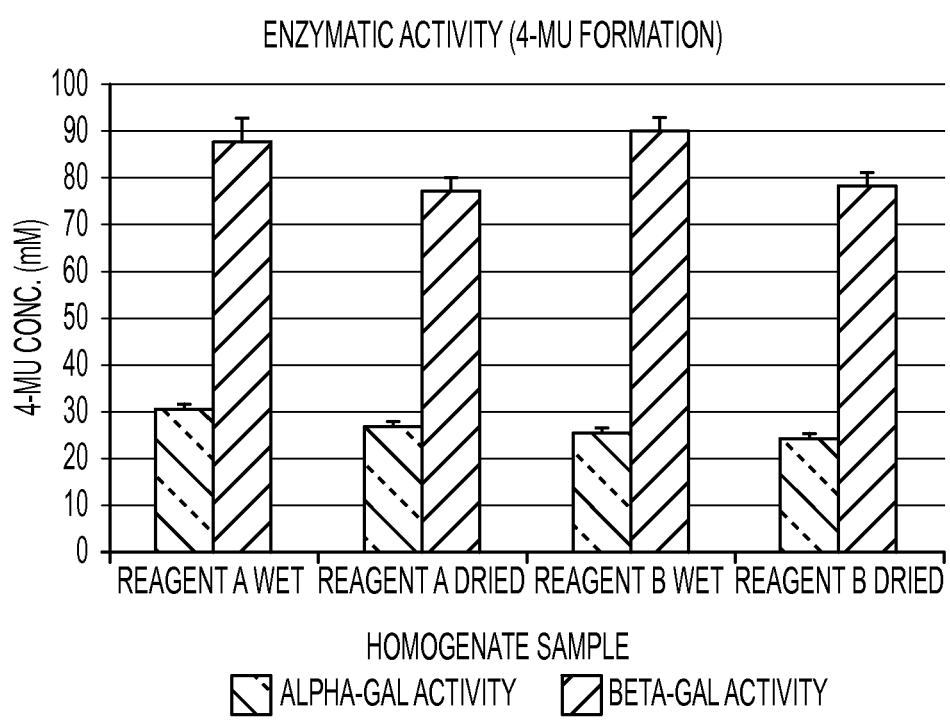
FIG. 5 shows comparison of enzymatic activity from wet and dried tissue homogenate.

Rat liver tissue (approx. 50 mg) was homogenized in two separate reagent mixtures, A: phosphate buffer saline with 0.5% Triton and B: 10 mM Tris, 1 mM EDTA with 0.5% Triton-X100. Enzymatic activity was compared for homogenate samples that remained wet and equivalent samples that were dried on filter paper (FIG. 5). Activities of alpha-galactosidase (alpha-GAL) and beta-galactosidase (beta-GAL) were measured by incubating at 37° C. for 2 hours with 4-methylumbelliferyl-alpha-D-galactopyranoside and 4-methylumbelliferyl-beta-D-galactopyranoside, respectively. 4-methylumbelliferone (4-MU) formation was measured by fluorescence. Activity levels were similar between wet and dried homogenization samples.

Figure 6:
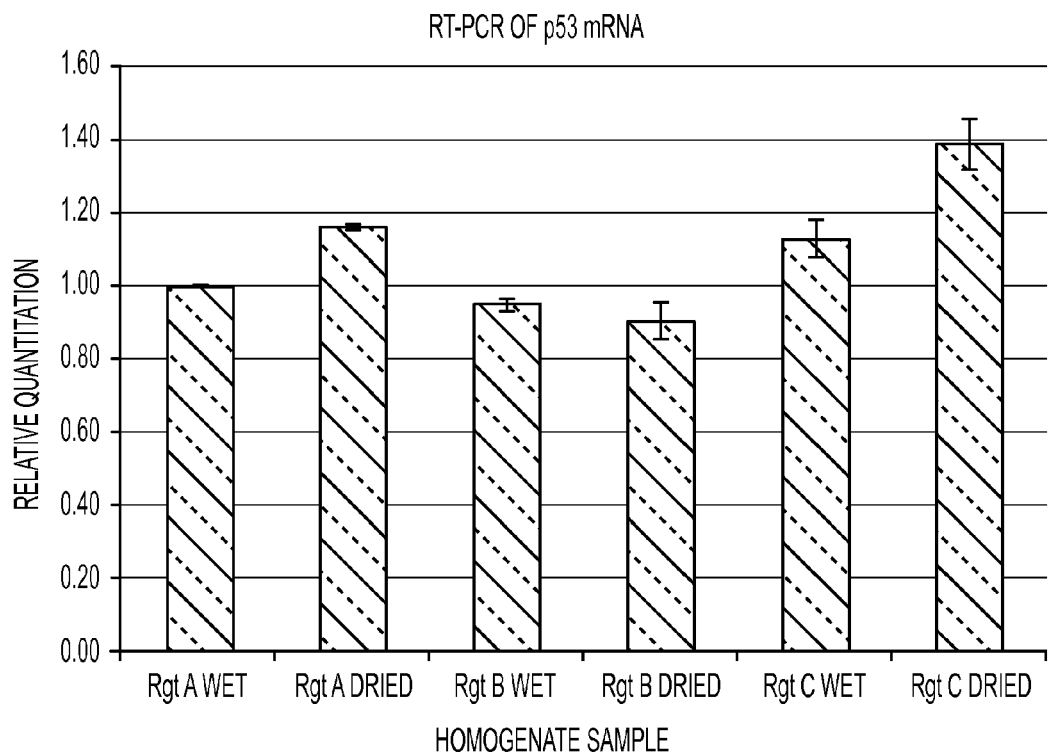
FIG. 6 shows comparison of p53 mRNA by RT-PCR from wet and dried tissue homogenate.

Three separate reagent mixtures were used to homogenize rat liver tissue, A: nuclease-free water B: nuclease-free water with 0.5% CHAPS and C: nuclease-free water with 0.5% Triton-X100. Portions of the homogenates were frozen while separate portions were applied to HemaSpot Devices and allowed to dry. Total RNA was isolated by standard Trizol methods and p53 mRNA levels for wet and dried homogenate were compared by RT-PCR using GAPDH as a reference gene (FIG. 6). Relative p53 mRNA levels were comparable between wet and dried samples on filter paper.

Figure 7:
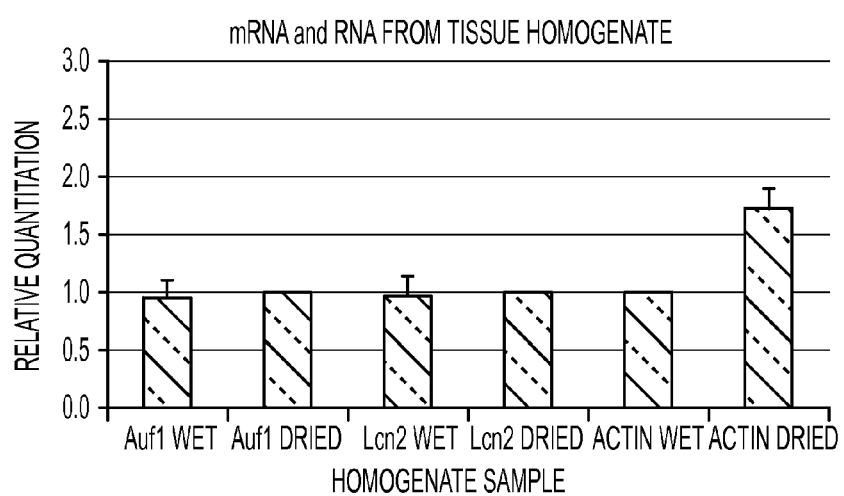
FIG. 7 shows relative quantitation by RT-PCR for mRNA and RNA from wet and dried samples.

Relative levels of mRNA Auf1 and Lcn2 and RNA Actin from homogenized rat liver tissue was measured by RT-PCR, using GAPDH as a reference gene (FIG. 7). Total RNA was isolated using standard Trizol methods from wet and filter-paper dried homogenates. Dried samples showed equal or higher relative levels of mRNA and RNA as compared to correlating wet samples.

The data set forth in FIGS. 5, 6 and 7 demonstrate the feasibility for accurately measuring protein and nucleotide levels from homogenates of tissue samples that have been dried on filter paper.

Together, these innovations will provide ideal preparation and storage of tissue specimens with minimal processing and refrigeration, while maintaining sample integrity for biomarker analysis. A commercial kit containing all required components would greatly simplify tissue collection and storage. The invention further provides a simplified, low cost tissue specimen preparation and storage method with minimal processing and refrigeration while maintaining sample integrity for analysis of biomarkers such as mRNA, miRNA, DNA, proteins and small molecules. A readily available commercial kit containing all required components would enable collection and analysis of tissues from remote and low resource areas, democratizing biospecimen collection and analysis. Availability of these stable, dried samples allow for simplified analysis of biomarkers to direct cancer treatments for the highest benefit and long-term storage in biorepositories would greatly aid disease and cancer research.

In the preceding detailed description, the invention is described with reference to specific exemplary embodiments thereof. Various modifications and changes may be made thereto without departing from the broader spirit and scope of the invention as set forth in the claims. The specification and drawings are, accordingly, to be regarded in an illustrative rather than a restrictive sense.

What is claimed is:

1. A method of extracting and storing a biological sample with a device, the method comprising:
    retrieving into the device a tissue sample from a specimen by extending a first plunger of the device;
    contacting the tissue sample with a buffer;
    homogenizing the tissue sample within the device by actuating a second plunger of the device to move a homogenization device attached to the second plunger to produce a liquid homogenate within the device;
    transferring the liquid homogenate on to an absorbent material; and
    drying the liquid homogenate on the absorbent material to create a storable sample at ambient temperature.

2. The method of claim 1, further comprising the step of subjecting a portion of the storable sample to testing.

3. The method of claim 1, wherein the homogenization device is selected from the group consisting of a grating device, a friction-based device, and a blade-based device.

4. The method of claim 1, wherein the buffer includes at least one aqueous buffer selected from the group consisting of: a phosphate buffer, a PBS containing protease inhibitor, an RNAse inhibitor, a detergent, and an organic solvent.

* * * * *